United States Patent
Akerfeldt et al.

(10) Patent No.: US 6,596,012 B2
(45) Date of Patent: Jul. 22, 2003

(54) INTRA-ARTERIAL OCCLUDER

(75) Inventors: Dan Akerfeldt, Nyvla (SE); Fredrik Preinitz, Uppsala (SE); Per Egneloev, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 09/836,529

(22) Filed: Apr. 18, 2001

(65) Prior Publication Data

US 2002/0019648 A1 Feb. 14, 2002

Related U.S. Application Data

(60) Provisional application No. 60/204,118, filed on May 15, 2000.

(30) Foreign Application Priority Data

Apr. 19, 2000 (EP) ............................................. 00850069

(51) Int. Cl.⁷ ............................................. A61B 17/08
(52) U.S. Cl. ...................................................... 606/213
(58) Field of Search ................................. 606/213, 215, 606/153, 232, 139, 157; 411/340; 114/197, 227; 433/25; 152/370; 4/286

(56) References Cited

U.S. PATENT DOCUMENTS

| 3,675,639 A | 7/1972 | Cimber |
| 3,874,388 A | 4/1975 | King et al. |
| 4,007,743 A | 2/1977 | Blake |

(List continued on next page.)

FOREIGN PATENT DOCUMENTS

| EP | 0 766 947 | 4/1997 |
| EP | 0 894 475 | 2/1999 |
| EP | 1 169 968 B1 | 1/2002 |
| JP | 57-24132 A | 5/1982 |
| JP | 2-307480 | 12/1990 |
| SU | 1088709 A | 4/1984 |
| WO | WO 90/14796 | 12/1990 |
| WO | WO 94/28800 | 12/1994 |
| WO | WO 99/40849 | 8/1999 |

OTHER PUBLICATIONS

Umit T. Aker et al., "Immediate Arterial Hemostasis After Cardiac Catheterization.", Catheterization and Cardiovascular Diagnosis vol. 31, pp. 228–232, 1994.

Terry D. King et al., "Nonoperative closure of atrial septal defects.", Surgery, vol. 75, No. 3, pp. 383–388, 1974.

James E. Lock et al., "Transcatheter Closure of Patent Ductus Arteriosus in Piglets.", The American Journal of Cardiology, vol. 55, pp. 826–829, 1985.

James E. Lock et al., "Transcatheter Closure of Atrial Septal Defects.", Circulation, vol. 79, No. 5, pp. 1091–1099, 1989.

Noel L. Mills et al., "Umbrella catheter for nonoperative closure of atrial septal defects.", Medical Instrumentation, vol. 12, No. 1, pp. 65–69, 1978.

(List continued on next page.)

Primary Examiner—David O. Reip
Assistant Examiner—D. Jacob Davis
(74) Attorney, Agent, or Firm—Foley & Lardner

(57) ABSTRACT

An intra-arterial occluder according to the invention exhibits a central elongated portion being comparatively stiff, e.g., by being thicker, and an outer rim portion being more flexible. The occluder is passed through the puncture, and is oriented such that the axis of the central portion is generally coaxial with the vessel. When retracted, the central portion will rest against the vessel wall at two diametrically opposed areas around the puncture, and along the length of the vessel. These areas represent the strongest areas around the puncture, and will therefore be able to safely carry the retracting force. At the same time, the thinner circumferential rim portion, which is easily foldable to fit into an insertion tool, adapts to the vessel wall and acts as an efficient sealing.

31 Claims, 3 Drawing Sheets

U.S. PATENT DOCUMENTS

| | | |
|---|---|---|
| 4,744,364 A | 5/1988 | Kensey |
| 4,852,568 A | 8/1989 | Kensey |
| 4,890,612 A | 1/1990 | Kensey |
| 4,917,089 A | 4/1990 | Sideris |
| 5,021,059 A | 6/1991 | Kensey et al. |
| 5,108,420 A | 4/1992 | Marks |
| 5,171,259 A | 12/1992 | Inoue |
| 5,192,302 A | 3/1993 | Kensey et al. |
| 5,342,393 A | 8/1994 | Stack .................. 606/213 |
| 5,350,399 A | 9/1994 | Erlebacher et al. ......... 606/213 |
| 5,531,759 A | 7/1996 | Kensey et al. |
| 5,620,461 A | 4/1997 | Muijs Van De Moer et al. .................. 606/213 |
| 5,700,277 A | * 12/1997 | Nash et al. .................. 60/213 |
| 5,725,577 A | 3/1998 | Saxon .................. 623/11 |
| 5,861,004 A | 1/1999 | Kensey et al. |

OTHER PUBLICATIONS

William J. Rashkind et al., "Nonsurgical closure of patent ductus arteriosus: clinical application of the Rashkind PDA Occluder System.", Circulation, vol. 75, No. 3, pp. 583–592, 1987.

William J. Rashkind, "Transcatheter Treatment of Congenital Heart Disease.", Circulation, vol. 67, No. 4, pp. 711–716, 1983.

* cited by examiner

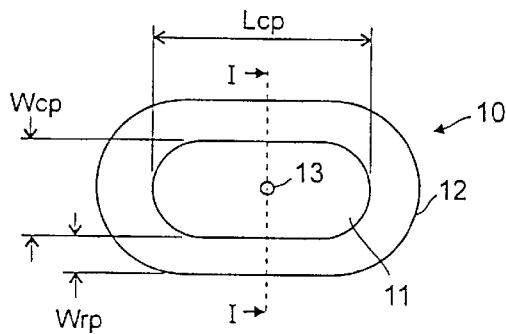
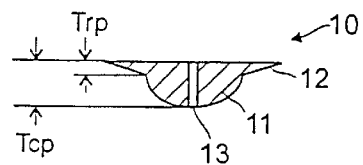
Fig. 1
Fig. 2
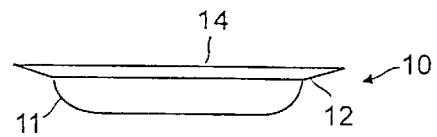
Fig. 3
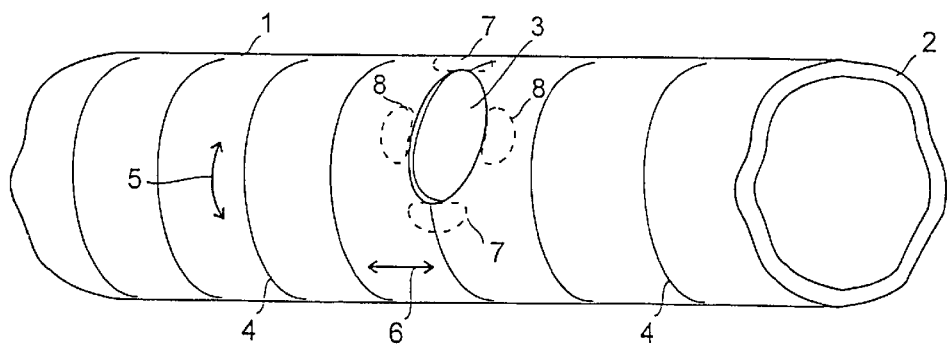
Fig. 4

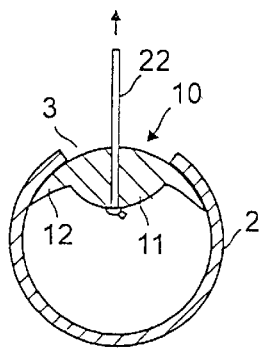
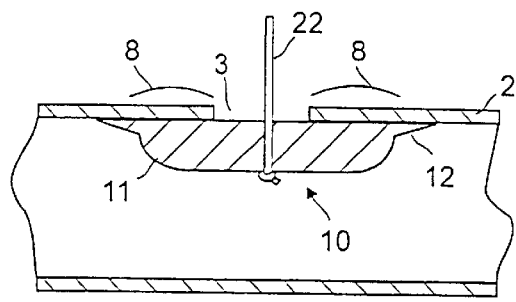
Fig. 5   Fig. 6
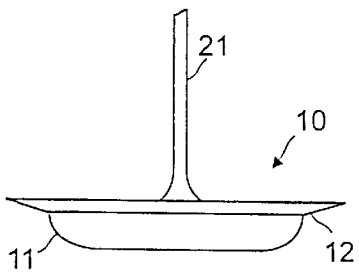
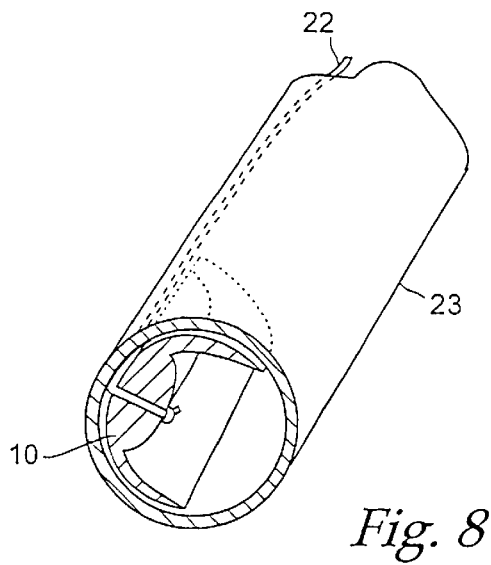
Fig. 7   Fig. 8
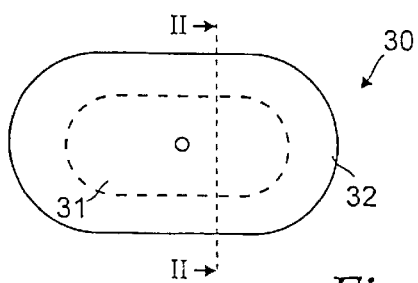
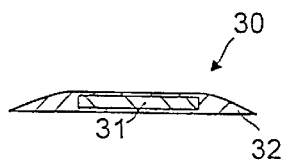
Fig. 9   Fig. 10

INTRA-ARTERIAL OCCLUDER

CROSS-REFERENCE TO PROVISIONAL APPLICATION

This application is based on, and claims priority to, provisional application No. 60/204,118, filed May 15, 2000, and European Application No. 00850069.6, filed Apr. 19, 2000.

TECHNICAL FIELD OF THE INVENTION

The present invention relates to a plug for sealing a percutaneous puncture in a vessel or artery, at the inner surface thereof.

BACKGROUND OF THE INVENTION

During certain types of medical surgery or treatment an introducer is used to access the vascular system of a patient. The introducer is inserted through the wall of a blood vessel in order to obtain access to the vascular system and may thereafter be used for guiding medical instruments such as catheters, guide wires and the like. After the completion of the medical procedure there will be an incision or a wound in the wall of the blood vessel corresponding to the size of the introducer. The bleeding from the wound, which is the result of such a surgical operation, may be stopped by applying direct pressure on the wound. However, applying direct pressure on the wound will require assistance of medical personnel and may also restrict the blood flow through the vessel.

EP-766 947 A2 describes a hemostatic puncture device for sealing a percutaneous puncture. The main parts of this device are an anchoring means, a collagen foam acting as a sealing means, a filament means and carrier means. The device uses an introducer or the like in order to guide the different parts to the puncture. The anchoring means, which is a narrow, rigid beam member, is introduced through the puncture to be inserted into the vessel. During the introduction, the anchoring means is in a longitudinal position, in order to fit into the introducer. In order to function as an anchor the anchoring means is manipulated in such a way that its end portions grip the inner edges of the puncture. The anchoring means is connected to the sealing means by the filament means in a pulley-like configuration. Thus, after the anchoring means has been put in place and the introducer is withdrawn the pulley-like configuration will pull the sealing means towards the puncture and then eventually seal the puncture on the outside wall of the vessel. Thus, the collagen foam performs all the sealing, i.e. the puncture is only sealed on the outside wall of the vessel. The collagen foam is effective in stopping the flow of blood, but the closure device according to EP-766 947 has disadvantages. One such disadvantage is the risk that the local tension applied to the edges of the puncture by the anchoring means, which contacts the puncture edge at two sites only, will rupture the edges of the puncture. In addition, the use of a sealing that seals on the outside of the vessel requires higher sealing force than a corresponding inner sealing.

Based on U.S. Pat. No. 5,350,399, it is known to seal a puncture through a vessel with an intra-arterial occluder and an extra-arterial occluder, respectively. The occluders are made of resilient biocompatible and/or bioabsorbable material and are held together by a saw-toothed guide extending from the intra-arterial occluder. A similar sealing is also disclosed in U.S. Pat. No. 5,342,393 wherein inner and outer rivet members are joined by a stem extending from the inner rivet to seal a puncture.

In addition, another intra-arterial occluder is described in U.S. Pat. No. 4,852,568.

However, when using an intra-arterial occluder there is still a problem in that the edge of the puncture might rupture when a retracting force is applied to the stem of the intra-arterial occluder in order to urge it against the vessel wall. In addition, the occluder according to U.S. Pat. No. 5,342,393 includes small hook-like means to clamp the edge of the puncture in order to ensure the sealing function of the occluders. These hook-like means are also a possible source for damage to the edge of the puncture.

Thus, there is a need for an improved intra-arterial occluder that provides a safe sealing of a percutaneous puncture, and at the same time reduces the risk of a rupture in the vessel wall when applying a retracting force to the intra-arterial occluder in order to urge the occluder against the vessel wall.

SUMMARY OF THE INVENTION

According to one aspect of the present invention, an occluder for intra-arterial sealing a puncture in a vessel or artery is provided, comprising: a first portion having a length exceeding a first diameter of the puncture in a direction along the vessel or artery and a width less than a second diameter of the puncture in a direction transverse to the vessel or artery, said first portion having longitudinal edges; and a second portion positioned at least along said longitudinal edges of said first portion, wherein said first portion has a higher structural stiffness than the second portion.

According to another aspect of the present invention, an occluder positioned on an interior of a blood vessel or artery for sealing a puncture is provided, comprising: a central portion; and a rim portion operatively connected with said central portion, wherein said central portion has a relatively greater stiffness than said rim portion.

Further, according to yet another aspect of the present invention, a method of sealing a puncture in a blood vessel or artery, comprising the steps of: inserting an occluder into the puncture to the interior of the blood vessel or artery, said occluder comprising: a first portion having a length exceeding a first diameter of the puncture in a direction along the vessel or artery and a width less than a second diameter of the puncture in a direction transverse to the vessel or artery, said first portion having longitudinal edges, and a second portion positioned at least along said longitudinal edges of said first portion, wherein said first portion has a higher structural stiffness than the second portion; and moving said occluder relative to said blood vessel to engage said occluder with an interior wall of the blood vessel or artery.

Further scope of applicability of the present invention will become apparent from the detailed description given hereinafter. However, it should be understood that the detailed description and specific examples, while indicating preferred embodiments of the invention are given by way of illustration only. Various changes and modifications within the spirit and scope of the invention will become apparent to those skilled in the art from this detailed description. Reference is made to the accompanying drawings, which are given by way of illustration only and thus are not limiting the present invention.

FIG. 1 is a front view of an embodiment of an intra-arterial occluder according to the present invention.

FIG. 2 is a cross sectional view taken along line I—I of FIG. 1.

FIG. 3 is a side view of the occluder of FIG. 1.

FIG. 4 is a schematic illustration of a puncture in a vessel.

FIG. 5 is a cross sectional view, perpendicular to the vessel, of an intra-arterial occluder according to the present invention sealing a puncture.

FIG. 6 is a cross sectional view, along the length of the vessel, of an intra-arterial occluder according to the present invention sealing a puncture.

FIG. 7 shows another embodiment of an occluder according to the invention.

FIG. 8 is a cross section of an introducer and an occluder disposed therein.

FIG. 9 is a front view of a second embodiment of an intra-arterial occluder according to the present invention.

FIG. 10 is a cross sectional view taken along line II—II of FIG. 9.

DETAILED DESCRIPTION OF PREFERRED EMBODIMENTS

Figure 11:
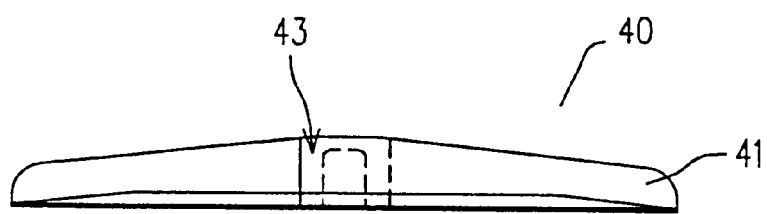
FIG. 11 is a side view of a third embodiment of an intra-arterial occluder according to the present invention.

In one aspect, the intra-arterial occluder according to the invention exhibits a central elongated portion, attached to a retracting means or retractor, said central elongated portion having a higher stiffness than a surrounding rim portion, in order to transfer the retracting force to those areas surrounding the puncture that have the highest strength against rupture. In a preferred embodiment, the higher stiffness is achieved by forming the central portion with a considerably higher thickness than the surrounding rim portion.

In use, the occluder is passed through the puncture, and is oriented such that the axis of the central portion is generally coaxial with the vessel. When retracted, due to its stiffness the central portion will rest against the vessel wall at two diametrically opposed areas around the puncture, and along the length of the vessel.

These areas represent the strongest areas around the puncture, and will therefore be able to safely carry the retracting force. At the same time, the less stiff circumferential rim portion, which is easily foldable to fit into an insertion tool, adapts to the vessel wall and acts as an efficient sealing.

Turning to the figures, in FIG. 4 is shown a portion of a vessel 1 in a living body, such as the femoral artery. A puncture 3 has been made through the vessel wall 2, thereby creating an opening which has to be occluded after the treatment that made the puncture necessary. Indicated in FIG. 4 is also the fibrous structure 4 of the vessel. This fibrous structure has the effect that the vessel is relatively strong in its circumferential direction 5. At the same time, the strength of the vessel fluctuates and is comparatively weak in its longitudinal direction 6.

Therefore, when applying a retracting force (i.e. a force acting on the edge of the puncture and being directed outward from the vessel) those areas 8 near the edge of the rupture that are situated along the axis of the vessel can withstand a higher tension than those areas 7 that are situated transversally thereto.

According to the invention, this circumstance can be utilized to form an improved intra-arterial occluder, an embodiment of such an occluder 10 being shown in FIGS. 1, 2 and 3, wherein FIG. 1 is a front view, FIG. 2 is a cross sectional view and FIG. 3 is a side view.

In general, the occluder 10 according to the invention comprises an elongated comparatively stiff central portion 11, surrounded by a rim portion 12 on at least the longitudinal sides of the central portion, said rim portion having a reduced stiffness with respect to the central portion. In addition, the occluder is provided with a generally flat surface 14, extending over the central portion and the rim portion, for contact with the inner wall of the vessel around the puncture, although this surface also could be provided with a certain degree of texture.

The dimensions of the occluder should be selected to suit the puncture to be sealed. As a guidance for practicing the present invention, some general recommendation on occluder dimensions are given below.

The central portion 11 has a longitudinal length Lcp that exceeds the diameter of the puncture in the vessel direction, taking the dimensions of the occluder introducing tool (as will be described below) into account since it is probable that the occluder inserting tool will widen the puncture to some extent. Preferably, the length Lcp of the central portion is about 50% longer than the diameter of the puncture in the vessel direction. A typical value of Lcp is about 6 mm.

At the same time, the width Wcp of the central portion should be less than the puncture diameter in the direction transverse to the vessel direction, in order to be safely inserted through the puncture in a folded state and to reduce the width of the abutment areas of the central portion against the vessel wall.

The rim portion 12 of lower stiffness could be formed as separate portions extending along each side of the central portion, although they are preferably formed as a surrounding continuous rim around the central portion (as shown in the figures).

In a preferred embodiment, as will be described below, the different stiffness of the central portion and the rim portion, respectively, is achieved by forming said portion as integrated sections having different thickness.

The reduced thickness of the rim portion, i.e. the lower stiffness, provides a flexibility to the rim portion that improves the sealing properties of the occluder.

The central portion 11 has a maximum thickness Tcp which gives the central portion an improved stiffness to carry a retracting load, while the rim portion 12 has a maximum thickness of Trp. Depending on the specific application, Trp is typically approximately ½ of Tcp or less, and preferably about ⅓ of Tcp. A typical value of Tcp is about 1 mm.

The width Wcp of the central portion 11 should be less than the inner diameter of the introducing tool used to insert the occluder in the vessel, in order to allow the occluder to be folded and placed within the introducing tool. The overall width of the occluder (i.e. Wcp+2*Wrp) is typically about 50% larger than the inner diameter of the introducing tool.

By inserting the occluder into the vessel in such a way that the respective end portions of the elongated central portion abut against the longitudinally situated puncture edge areas 8 of the inner vessel wall, a retracting force applied to the occluder will mainly be absorbed by those areas 8 having the highest strength against rupture. Preferably, the rim portion is tapered outwards towards its periphery in order improve its flexibility and to provide an essentially step free inner junction against the vessel wall.

When urging the intra-arterial occluder towards the inner wall of the vessel, the rim portion covers the areas surrounding the puncture, thereby sealing the puncture against blood penetration. Due to the elongated shape of the occluder, i.e. its extension along the length of the vessel, a considerably more safe sealing will be obtained compared to a conventional circular sealing.

In addition, the elongated shape of the present occluder provides a self-guiding effect in that the outer ends of the occluder will align themselves in the vessel as they are drawn towards the vessel wall.

The position of an inserted occluder according to the invention is generally shown in the cross sectional views of FIGS. 5 and 6, shown a crosswise (FIG. 5) and a lengthwise (FIG. 6) section. The occluder 10 abuts against the vessel wall 2 due to a retracting force in the retractor 22. The rim portion 12 seals the puncture, and the ends sections of the central portion 11 rests against the comparatively strong areas 8, as described above.

Preferably, the central portion and the rim portion are integrated, allowing for easy one-step manufacturing.

Structure for applying the retracting force is provided in the central portion of the occluder. For example, as is shown in FIGS. 1, 2, 5 and 6, a through hole 13 is provided through which a string 22 could be passed and secured with a knot, a drop of an adhesive, melted plastic, or any other appropriate structure. The occluder is urged towards the vessel wall by simply pulling the string. In FIG. 7 is shown another embodiment of a pulling device, namely a stem 21 protruding from the central portion 11 of the occluder 10. The stem is integrally formed with the occluder, and could optionally be provided with a saw-tooth profile (not shown) for mating with an optional extra-arterial occluder.

An occluder according to the invention is typically manufactured by injection molding, and is formed of any suitable flexible and biodegradable material.

The intra-arterial occluder and its retractor are inserted into the vessel using an insertion tool similar to any suitable conventional tool, such as a tool described in any of the prior art documents referred to above. Thus, as is illustrated in FIG. 8, the occluder 10 according to the invention is folded along its longitudinal direction and is, together with its retractor 22, inserted into a generally tubular tool 23. Then, the tool is inserted through the puncture and the occluder is pushed out completely into the vessel with its longitudinal direction essentially in the longitudinal direction of the vessel. The tool is removed and, using the retractor, the occluder is urged against the inner vessel wall thereby sealing the puncture to stop blood from exiting through the puncture.

The pulling force of the retractor is maintained by any conventional means such as an adhesive applied to the skin of the patient (as described in U.S. Pat. No. 4,744,364) or an extra-arterial occluder (as described in U.S. Pat. No. 5,350, 399 and U.S. Pat. No. 5,342,393).

Thus, with an occluder according to the present invention, a tight sealing of a puncture in a vessel can be obtained. With the occluder of the invention, a lower sealing force is required compared to a case of a sealing means outside the vessel, since the blood pressure in the vessel acts on the occluder to urge it against the vessel wall.

The elongated structure of the occluder of the present embodiment, with its elongated thick central portion, ensures improved safety from ripping the edge of the puncture. At the same time, it is readily foldable for insertion into an introducer.

Although shown having a generally oval shape, the outer shape of the occluder could be any elongated shape ensuring a proper sealing of the puncture and, at the same time, allowing the thicker central portion to rest at the comparatively strong areas around the puncture, depicted with 8 in FIG. 4, or an essentially symmetrical shape as circular. However, the oval shape is preferred since it is assessed to limit the risk of injuring the vessel wall.

The difference in stiffness between the central portion and the rim portion of the occluder could also be achieved by other means than different thickness. For example, a second embodiment of an occluder 30 according to the present invention is shown in FIGS. 9 and 10, wherein the rim portion 32 is similar to the rim portion 12 of the first embodiment, but the higher stiffness of the central portion 33 is achieved with an insert 31 of a relatively more stiff bioabsorbable material than the material of the rim portion 32. Of course, the central portion could be made entirely of the material having higher material stiffness (i.e. the stiffer material not being an insert but forming the central portion in itself, in which case the rim portion should be separate and attached to the central portion for example with an adhesive.

Figure 12:
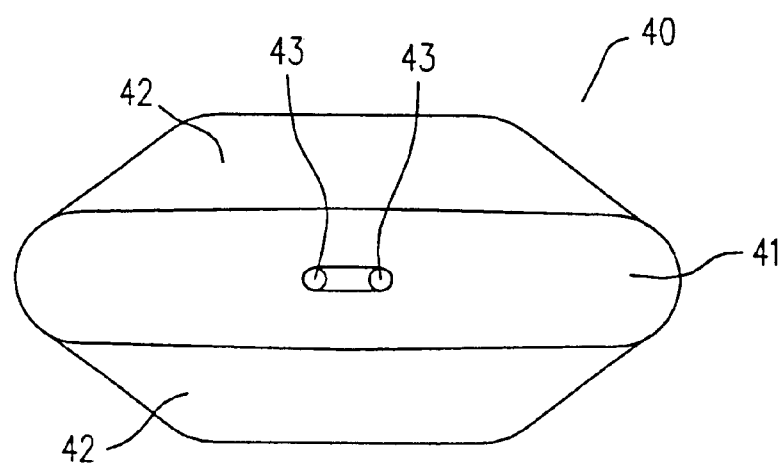
FIG. 12 is a top view of the third embodiment of the intra-arterial occluder according to the present invention.
Figure 13:
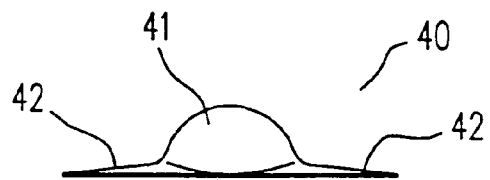
FIG. 13 is a front view of the third embodiment of the intra-arterial occluder of FIG. 11.

In FIGS. 11 to 13 a third embodiment of an occluder of the invention is illustrated.

The occluder 40 according to this embodiment comprises an elongated comparatively stiff central portion 41. The shape of this portion 11 is such that it is slightly wider at the middle than at the ends, and also it is slightly thicker at the middle than at the ends, as can be clearly seen in FIGS. 11 and 12. Furthermore, there are flexible side wings 42, which are substantially thinner than the central portion 41. This enables bending of the wings 42 towards each other to form an essentially cylindrical like structure, fitting into a cylindrical tool, like the one disclosed in FIG. 8. However, the occluder illustrated in FIG. 8 is bent or folded in an opposite manner compared to the manner the occluder according to the third embodiment should preferably be folded.

A retaining structure, e.g. a suture, is secured to the occluder by passing it through holes 43 in the thickest part of the central portion 41.

It is clear that the present invention may be varied in many ways with respect to the detailed description above. Such variations are not to be regarded as a departure from the spirit and scope of the invention, and all such modifications as would be clear to one skilled in the art are intended to be included within the scope of the following claims. For example, as alluded to above, an outer element may be positioned in the puncture, relative to the exterior of the blood vessel or artery. The invention may be applied to other types of vessels or arteries as well.

The contents of U.S. provisional application No. 60/204, 118, filed May 15, 2000, and the contents of European Patent Application No. 00850069.6, filed Apr. 19, 2000, are each hereby incorporated by reference in their entirety.

We claim:

1. An occluder for intra-arterial sealing a puncture in a vessel or artery, comprising:
   a first portion having a length exceeding a first diameter of the puncture in a direction along the vessel or artery and a width less than a second diameter of the puncture in a direction transverse to the vessel or artery, said first portion having longitudinal edges; and
   a second portion positioned at least along said longitudinal edges of said first portion,
   wherein said first portion has a higher structural stiffness than the second portion.

2. The occluder of claim 1,
   wherein said first portion further comprises latitudinal edges, said longitudinal edges being longer than said latitudinal edges.

3. The occluder of claim 2, wherein said first portion is substantially centered relative to said second portion.

4. The occluder of claim 3, wherein said second portion surrounds said first portion.

5. The occluder of claim 4, wherein at least one of said first and second portions has a substantially oval shape.

6. The occluder of claim 4, wherein each of said first and second portions has a substantially oval shape.

7. The occluder of claim 2, wherein said first portion has a first maximum thickness and said second portion has a second maximum thickness, said first maximum thickness being at least twice the second maximum thickness.

8. The occluder of claim 7, wherein said first maximum thickness is at least three times the second maximum thickness.

9. The occluder of claim 2, wherein said first portion comprises a first material and said second portion comprises a second material different from said first material, said first material having a higher material stiffness than said second material.

10. The occluder of claim 9, wherein said first portion comprises an insert as said first material, said insert being inserted into said second material.

11. The occluder of claim 2, wherein each of said first and second portions are made of bioabsorbable material.

12. The occluder of claim 2, wherein at least one of said first and second portions has a substantially oval shape.

13. The occluder of claim 12, wherein said second portion comprises tapered outer edges.

14. The occluder of claim 13, wherein said first portion has a first maximum thickness and said second portion has a second maximum thickness, said first maximum thickness being at least twice the second maximum thickness.

15. The occluder of claim 2, wherein said length of said first portion is at least fifty percent (50%) greater than said first diameter of the puncture.

16. The occluder of claim 15, wherein said length of said first portion is approximately fifty percent (50%) greater than said first diameter of the puncture.

17. The occluder of claim 2, wherein said first and second portions are integrally formed of a single-piece structure.

18. The occluder of claim 2, further comprising a retractor for moving said first and second portions relative to said puncture.

19. The occluder of claim 18, wherein said retractor comprises a suture.

20. The occluder of claim 19, wherein said first portion comprises at least one hole for engagement with said retractor.

21. The occluder of claim 20, wherein said retractor extends through said hole and includes a knot positioned on an inner side of said first portion.

22. The occluder of claim 18, wherein said first portion, said second portion, and said retractor are integrally formed of a single-piece structure.

23. An occluder positionable on an interior of a blood vessel or artery for sealing a puncture, comprising:
  a central portion having a length and a width and a thickness, the central a portion being elongated in the length direction; and
  a rim portion operatively connected with said central portion,
  wherein said central portion has a relatively greater stiffness than said rim portion.

24. An occluder positionable on an interior of a blood vessel or artery for sealing a puncture, comprising:
  a central elongated portion; and
  a rim portion operatively connected with said central portion,
  wherein said central portion has a relatively greater stiffness than said rim portion;
  wherein said central portion has an elongated shape with longitudinal and latitudinal edges, said longitudinal edges being longer than said latitudinal edges,
  wherein said longitudinal edges have a length greater than a diameter of the puncture in a direction along the blood vessel or artery.

25. The occluder of claim 24, wherein at least one of said central portion and said rim portion has a substantially oval shape.

26. The occluder of claim 24, wherein said central portion has a greater thickness than said rim portion.

27. The occluder of claim 24, wherein said central portion is made of a first material and said rim portion is made of a second material different from said first material, said first material having a material stiffness greater than that of said second material.

28. A method of sealing a puncture in a blood vessel or artery, comprising the steps of:
  inserting an occluder into the puncture to the interior of the blood vessel or artery, said occluder comprising:
    a first portion having a length exceeding a first diameter of the puncture in a direction along the vessel or artery and a width less than a second diameter of the puncture in a direction transverse to the vessel or artery, said first portion having longitudinal edges, and
    a second portion positioned at least along said longitudinal edges of said first portion,
    wherein said first portion has a higher structural stiffness than the second portion; and
  moving said occluder relative to said blood vessel or artery to engage said occluder with an interior wall of the blood vessel or artery.

29. The method of claim 28, wherein at least one of said first portion and said second portion has a substantially oval shape.

30. The method of claim 28, wherein said first portion has a greater thickness than said second portion.

31. The method of claim 28, wherein said first portion is made of a first material and said second portion is made of a second material different from said first material, said first material having a material stiffness greater than that of said second material.

* * * * *